United States Patent [19]

Chang et al.

[11] Patent Number: 4,651,280

[45] Date of Patent: Mar. 17, 1987

[54] ELECTROSURGICAL CONTROL SYSTEM USING TISSUE CONDUCTIVITY

[76] Inventors: Sien S. Chang, 1st Fl. No. 171, East Division, Veterans General Hospital, Taipei, Taiwan, 111; Shuenn T. Young, 3rd Fl. No. 46, Lane 45, Sec. 1, Min Deng Rd., Ruey Fang Town, Taipei County, Taiwan, 224

[21] Appl. No.: 806,139

[22] Filed: Dec. 11, 1985

Related U.S. Application Data

[63] Continuation of Ser. No. 491,225, May 3, 1983, abandoned.

[51] Int. Cl.⁴ ............................ A61B 17/36; A61B 17/39; G06F 15/42
[52] U.S. Cl. ................................ 364/413; 128/303.14; 128/734
[58] Field of Search ................ 364/413, 415; 128/305, 128/311, 303.13, 303.14, 303.17, 734

[56] References Cited

U.S. PATENT DOCUMENTS

| | | | |
|---|---|---|---|
| 3,601,126 | 8/1971 | Estes | 128/303.14 |
| 4,126,137 | 11/1978 | Archibald | 128/303.14 |
| 4,231,372 | 11/1980 | Newton | 128/303.17 X |
| 4,232,676 | 11/1980 | Herczog | 128/303.14 |
| 4,281,373 | 7/1981 | Mabille | 128/303.17 |
| 4,416,277 | 11/1983 | Newton et al. | 128/303.13 |
| 4,494,541 | 1/1985 | Archibald | 128/303.13 |
| 4,498,475 | 2/1985 | Schneiderman | 128/303.14 |

OTHER PUBLICATIONS

Horowitz, P. et al., *The Art of Electronics*, Cambridge University Press, 1980, 118–119.
Peatman, J. *Microcomputer-Based Design*, McGraw-Hill, Inc., 1977, 92–95.

*Primary Examiner*—Jerry Smith
*Assistant Examiner*—Clark A. Jablon
*Attorney, Agent, or Firm*—Holman & Stern

[57] ABSTRACT

A Microprocessor controlled Relay is between and in series with the Electro-Surgical Unit and the NiCr loop, to control the output power of the E.S.U. during the operation of Transurethral Resection. The predetermined parameters may input to the Microprocessor for precision control of the E.S.U.. A current probe is connected to the output cable of the E.S.U. to take the variety of the output current of the E.S.U.. The E.S.U. output power will vary according to the variety of the load. By the differences of tissues, the differences of inclusions make the consistency and conductivity vary. The differences of conductivity make the load vary during operating procedure of Transurethral Resection. In other words, the control system can distinguish what tissue is resected according to the variety of the output power of the E.S.U..

6 Claims, 13 Drawing Figures

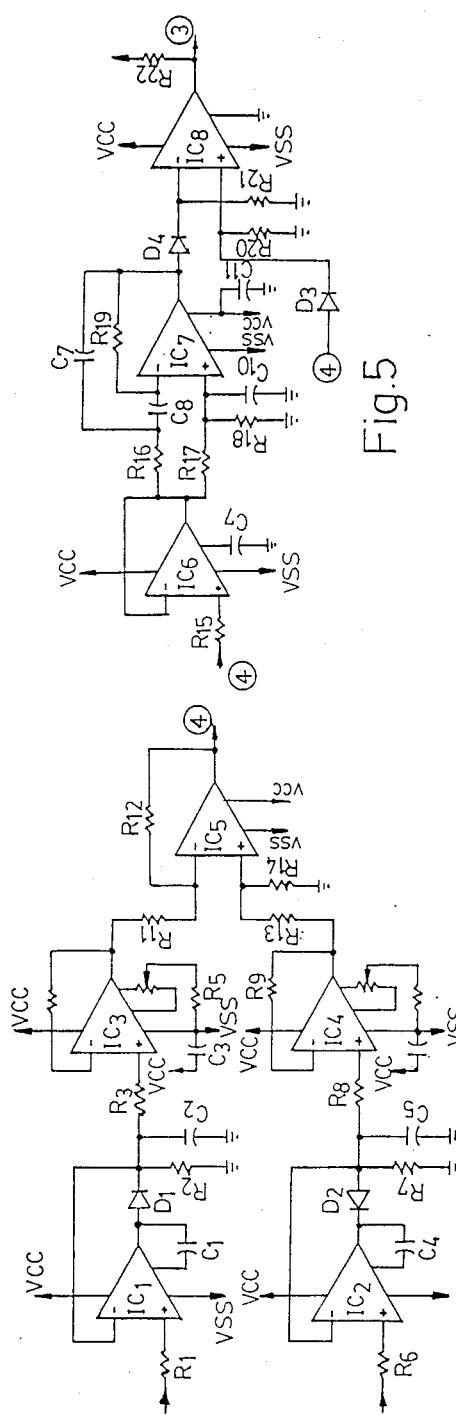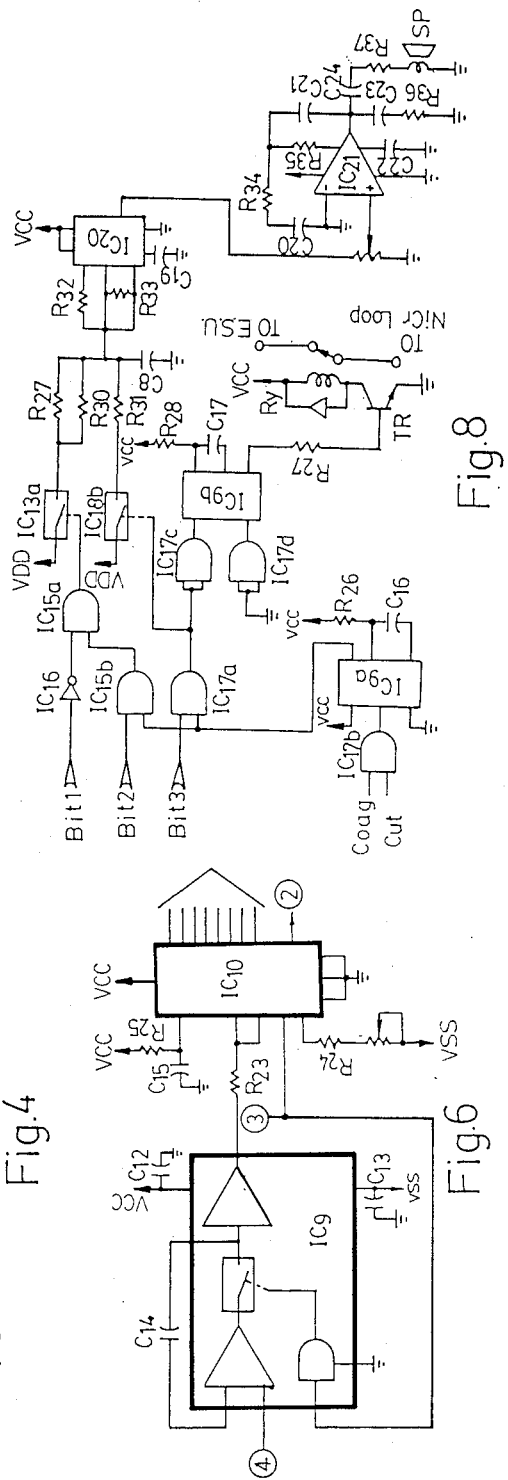
Fig.5
Fig.4
Fig.6
Fig.8

ELECTROSURGICAL CONTROL SYSTEM USING TISSUE CONDUCTIVITY

This is a continuation of application Ser. No. 491,225, filed May 3, 1983, and now abandoned.

BACKGROUND OF THE INVENTION

The present invention relates to an Electrosurgical Unit (E.S.U.) control and alarm circuit and, in particular, to circuits employing a current probe which takes variations in the E.S.U. output current due to different load conditions, then processes input current, and controls a cutting device, a Ni-Cr loop, usually so as to prevent the cutting of tissue and various bodily materials desired to be kept intact, while allowing the cutting of tissue and bodily materials desired to be cut.

It usually takes approximately four years of surgical training to perform a Transurethral Resection (TUR). If a control system is used, the training time will be reduced and the surgical operation itself will be much safer.

SUMMARY OF THE INVENTION

It is an object of the present invention to provide an automatic control system which will aid a surgeon in performing a TUR more safely and perfectly than ever. The underlying principle of the control system is that different tissues have various different resistance values and, consequently, conductivity may also vary. The output power of the ESU will vary accordingly during the operating procedure of a TUR.

The foregoing and other objects of the invention are accomplished by providing a means of applying a Microprocessor-Controlled Relay in a series between the ESU and the load (Adenoma, for example). The current probe is coupled with the input of a peak detector for current sensing. The peak detector is connected to a phase shifter so as to detect the peak of the input current. A level detector is directly connected to the outputs of the peak detector and of the phase detector and provides a control signal to the Sample/Hold circuit for data sampling and holding the data stable. The stable data is converted by an Analog/Digital Converter (A/D Converter) into a digital byte for processing by a Microprocessor. The Parallel Input/Output (PIO) circuit between the Central Processing Unit (CPU) and the A/D Converter serves as a buffer for the output of the A/D Converter to the CPU and supplies an adequate current for driving an alarm circuit and a Relay to cut off power to the ESU. The Read Only Memory (ROM), which is connected to the CPU through the data bus, stores the control program for use in performing desired control functions. A keyboard and display are connected through a controller to the CPU which is responsible for data processing, keyboard scanning, and display scanning.

BRIEF DESCRIPTION OF DRAWINGS

The present invention will be more readily understood with reference to drawings and accompanying descriptions.

FIG. 4 is a circuit diagram of the peak detector and summing circuit included in the control system of FIG. 3;

FIG. 5 is a circuit diagram of the Phase Shifter and Comparator included in the control system of FIG. 3;

FIG. 6 is a circuit diagram of the Sample/Hold circuit and A/D converter included in the control system of FIG. 3;

FIG. 8 is a circuit diagram of the peripheral device and alarm circuits included in the control system of FIG. 3;

DESCRIPTION OF THE PREFERRED EMBODIMENT

Figure 1:
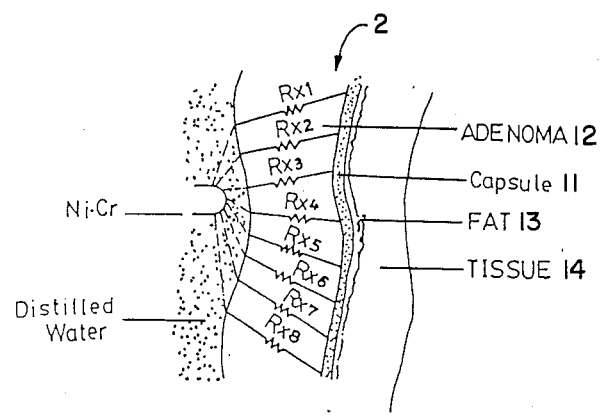
FIG. 1 is a schematic view, partially in section, illustrating the application of a cutting device to a prostate gland.
Figure 2:
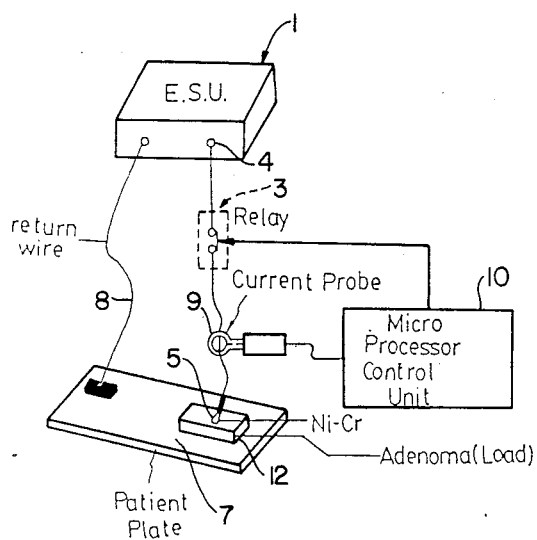
FIG. 2 is a schematic diagram illustrating the total system of the present invention.

In reference to FIGS. 1–13 of the accompanying drawings, these is shown an embodiment of a control system for an Electrosurgical Unit (ESU) 1 according to the present invention. In FIG. 1 is shown a cross section of tissue types 2. In FIG. 2, a relay 3 is connected in a series between an output from the output port 4 of the E.S.U. and a cutting device - Ni-Cr loop 5 or output electrode 5. Also, a load 12 (i.e. the Adenoma of the prostate gland) presented to the ESU is circuited by a patient electroplate 7, or return electrode 7, and a return wire 8 leading to the return port. A current probe 9 is attached near the surface of the output cable of the E.S.U. in order to take variations of the output current and transmit them to the Microprocessor Control Unit 10 (M.C.U.). The Microprocessor 10 processes the variation of the output current of the E.S.U. 1 and controls the ON/OFF of the Relay 3. In other words, ON/OFF of the E.S.U. is controlled by the M.C.U. 10 according to variation in the load, which will be described later. The variation in conductivity of the circuit makes the load current vary during the operating procedure of a transurethral resection (TUR).

During the surgical procedure of a TUR, the Ni-Cr loop 5 of the E.S.U. may come into contact with distilled water, Adenoma 12, capsule, and a little fat outside the prostate gland. In FIG. 1 there is shown a simplified cross-sectional view of the prostate gland 2. Surrounding the gland is a fibroelastic capsule 11, which is constructed of netted fibrous tissue 14 and contains few electrolytes; inside the capsule, the irregular, soft, and fluffy tissue is Adenoma 12, 2, which contains many electrolytes (low resistance). The compact construction of large particles is fat, 13 (high resistance). It is to be expected that the E.S.U. output power will vary according to the variation in the load. Because of differences in tissue, the resulting differences in inclusions make consistency and conductivity vary. The resistance of the compact fibroelastic capsule, which contains few electrolytes, is high. The resistance of the fat, which contains few electrolytes, is high also, while the resistance of the loose, irregular, fluffy tissue, which contains many electrolytes is low. The differences in conductivity make the load vary during the operating procedure of a TUR. In other words, we can make use of variations in output power of the E.S.U. to determine what tissues will be resectioned (cut) and to prevent the cutting of others if desired.

In reference to FIG. 1, with the Ni-Cr loop 5 inside the prostate gland, being merged in the Adenoma 12, the resistance between the Ni-Cr loop and the capsule is much lower than it would be with a combination of Ni-Cr and capsule (high ohms) or Ni-Cr and fat (high resistance). There is an infinite number of equivalent resistive Adenoma links in parallel between the Ni-Cr loop and the capsule (according to Ohms's Law, resistive links in parallel will reduce the total resistance). In other words, the output power of the E.S.U. is (desired) high when in the low resistance-high conductivity Adenoma and the sensing current of the current probe is high also. On the contrary, the output power of the E.S.U. is (desired) low when in the high resistance-low conductivity of the capsule and the sensing current of the current probe is also low. The present invention can automatically determine whether the input current belongs to the Adenoma condition or to the capsule condition. When the Ni-Cr loop touches the capsule, the alarm system will be ON and the output power of the ESU will be cut off. Therefore, during the operation of a TUR, the use of this control system increases safely and decreases surgical training time and operating room time. Furthermore, any surgeon using the ESU with the help of the described control system will execute the operation of a TUR perfectly and completely.

Figure 3:
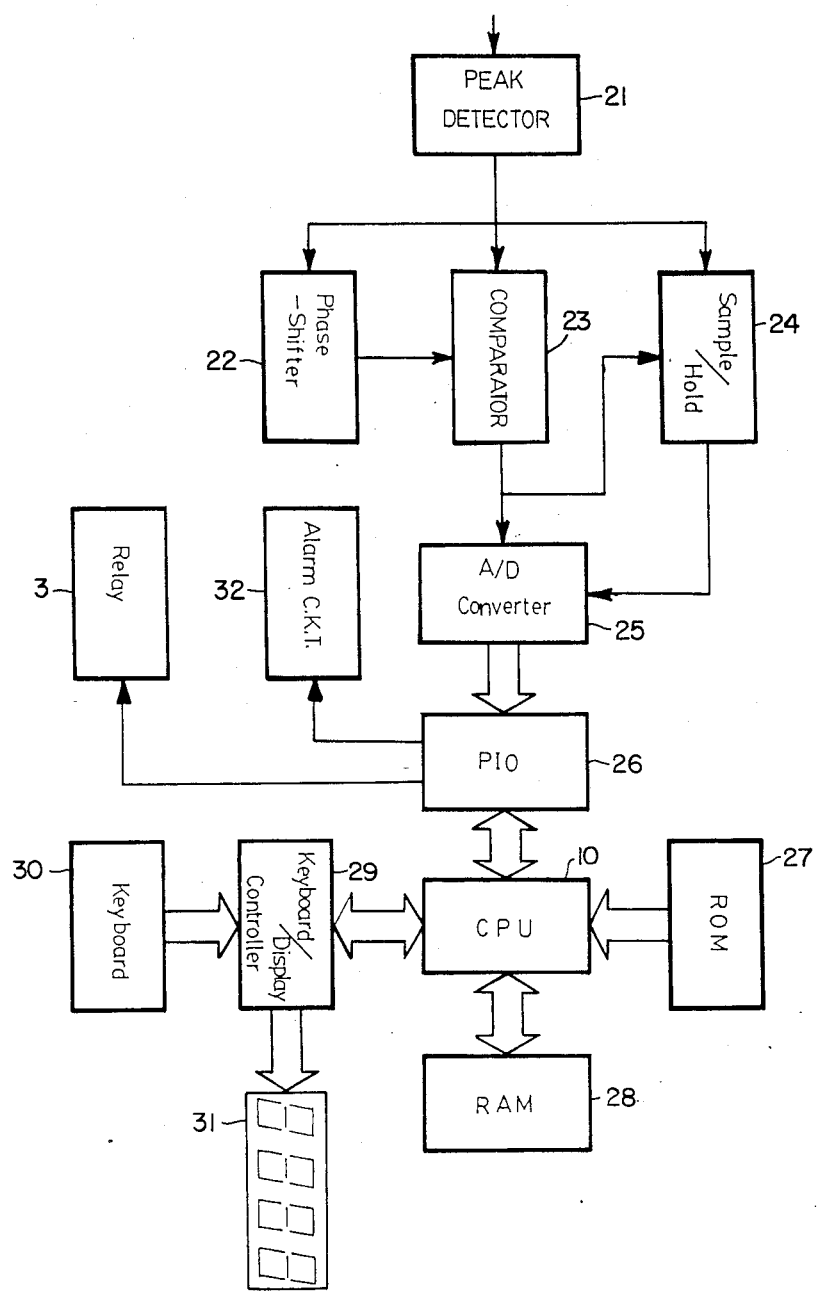
FIG. 3 is a block diagram of one embodiment of the control system of the present invention.

The control system will be described as follows;

in the embodiment of FIG. 3 there is shown a block diagram of the whole control system. A current probe is used to pick up the variation in the output current. A peak detector 21 detects the level of the input current coming from the current probe. In order to generate a control pulse, a Phase Shifter 22 is used to shift the input current phase, producing a current which lags behind the original current. At a later stage, the lagging current and the original current can be compared to each other at the time of the respective peak. The Comparator 23 compares the original current and the current after being phase-shifted. The Sample/Hold circuit 24 holds the data stable for microprocessor use. The A/D Converter 25 is necessary for analog to digital cnversion. PIO (Parallel Inut/Output) 26 is included as an interface between the CPU 10 and peripheral devices. The CPU 10 is provided for executing logical operations and for processing and analyzing data which controls the desired devices. Read Only Memory (ROM) 28 stores a fixed control sequence (software). Random Access Memory (RAM) stores temporary data which can be changed at any time. The Keyboard/Display Controller 29 scans the keyboard 30 and display 31, encodes and provides binary data for microprocessor use, and encodes binary data for seven segment display. The display serves to disply any parameters in decimal form. The keyboard is provided for the input of parameters into the microprocessor.

In reference to FIG. 4, there is shown a peak detector and summing circuit which includes five operational amplifiers, IC 1–IC 5. IC 1 and IC 2 are buffers and have very high impedance so as to increase the (signal-to-noise) S/N ratio. Positive signals pass through IC 1, negative signal pass through IC 2; and IC 3 and IC 4 amplify these signals.

In reference to FIG. 5 there is shown a phase shifter and a comparator which includes IC 6–IC 8. The voltage follower IC 6 isolates the input signal to the phase shifter. The phase shifter includes IC 7, R16–R19, and C 8–C 10 and shifts the input signal a few degrees behind the original. IC 8 is a comparator which is used to compare the input signal with the phase-shifted signal. Any time the peak appears, a control pulse will be generated to control the Sample/Hold circuit.

FIG. 6 is a circuit diagram of the Sample/Hold circuit and the (analog-to-digital) A/D Converter. Pin 2 of IC 9 is a sampling control pin. Capacitor C 14 holds the sampling signal until the signal is stable, then the A/D Converter changes this signal into binary data. The A/D Converter consists of IC 10, R23–R25, C 15 and its function is to convert the analog signal into eight bit binary data for microprocessor use.

Figure 7:
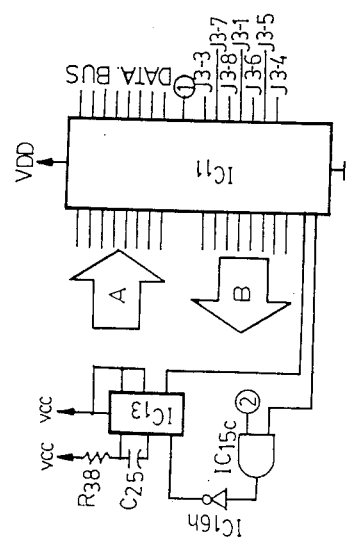
FIG. 7 is a Parallel Input/Output circuit included in the control system of FIG. 3.

FIG. 7 is a PIO (Parallel Input/Output Circuit) which includes two I/O ports. Port A transfers data from the A/D Converter to the CPU and port B latches the data, controls the ON/OFF of the output power of the ESU, and the ON/OFF of the alarm circuit.

FIG. 8 is a circuit diagram of the peripheral device and alarm circuits which are interfacing circuits and include IC 15-IC 21. IC 17b and IC 19a are used to extend the duration of pulse of the resultant signal from the coagulation and cutting signals. The resultant signal is then logically combined with bits 2 and 3 of the CPU data bus to form a control signal for the Relay circuit and Alarm circuit. Analog switches IC 18a and IC 18b are controlled by bits 1, 2, and 3 of the CPU. IC 19b enlarges the width of the signal from IC 17a to let the Relay operate properly. Alarm circuit IC 20 functions as an alarm signal generator and outputs the signal to the Audio Amplifier IC 21, drives a speaker to produce two separate tones for different tissues as shown on FIG. 8. IC 19b controls the Relay so as to control the output power of the E.S.U.

Figure 9:
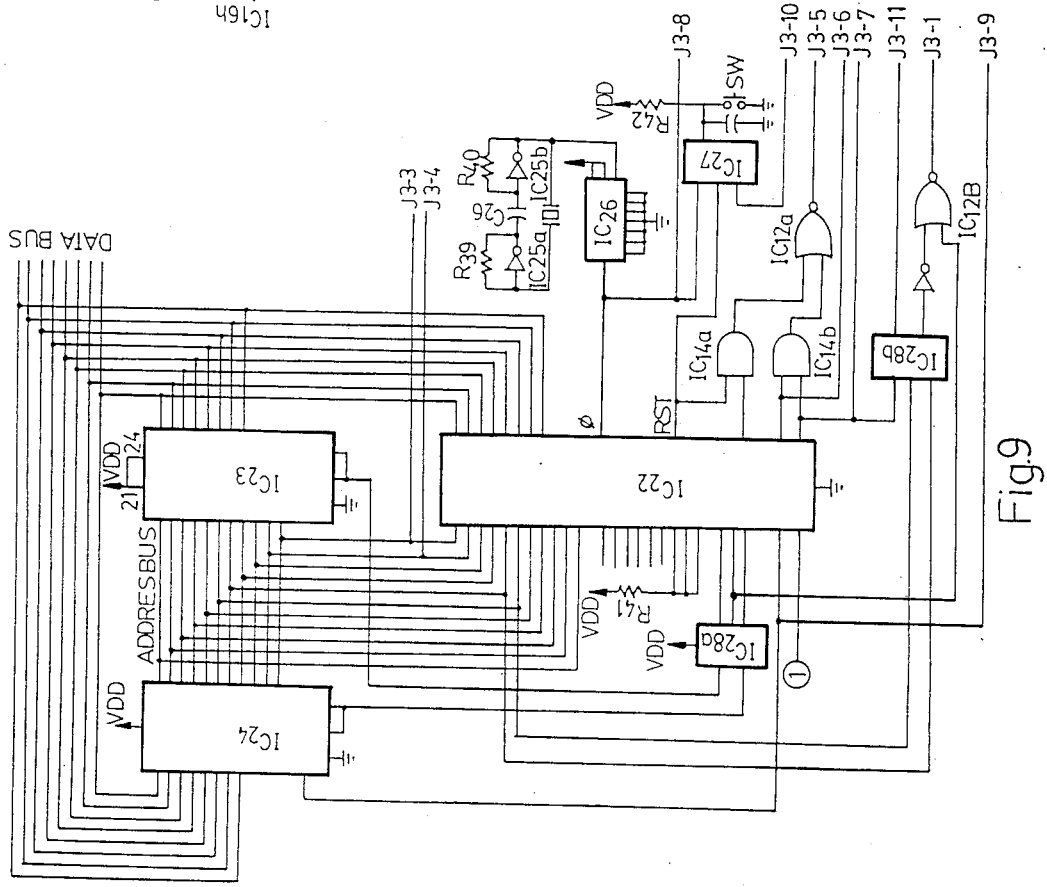
FIG. 9 is a circuit diagram of the CPU, ROM, RAM, and the clock generator included in the control system of FIG. 3.

FIG. 9 is a circuit diagram of the Central Processing Unit (CPU), Read Only Memory (ROM), Random Access Memory (RAM), and the Clock Generator circuit. The CPU executes logical operation and data transference. The controlling sequence is controlled by the program stored in ROM and temporary data is stored in RAM. The Clock Generator generates the clock pulse for CPU use. The Clock Generator is comprised of IC 25a, IC 25b, resistors R39 and R40, capacitor C26 and a (quartz) crystal. IC 26 divides and lowers the frequency of the output from the clock generator for CPU use.

Figure 10:
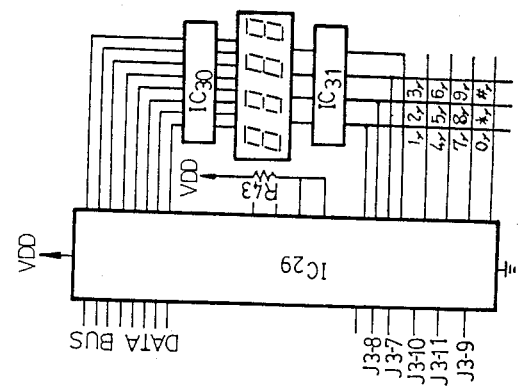
FIG. 10 is a circuit diagram of the Keyboard/Display controller, driver, and display included in the control system of FIG. 3.

FIG. 10 is a circuit diagram of the Keyboard/Display Controller in which IC 29, an integrated circuit, scans the keyboard and display, and encodes data. IC 30 and IC 31 serve as a current driving device which provides sufficient current for the seven segment display-Light Emitting Diode (LED). The seven segment display can display the parameters in the CPU, the programs stored in ROM, and the data stored in RAM.

Figure 11:
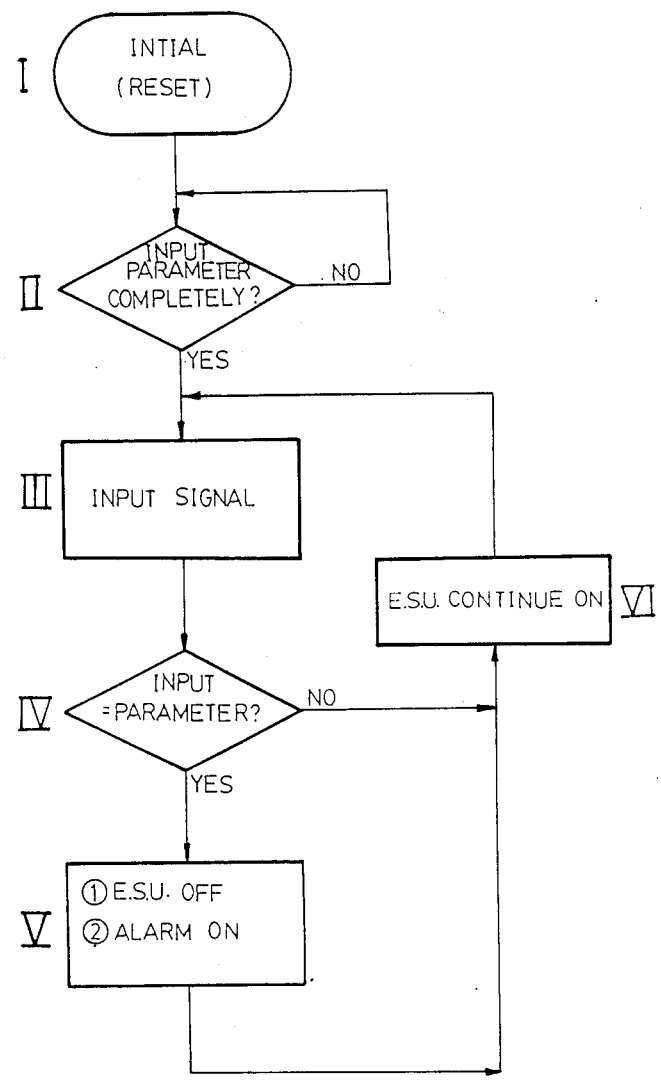
FIG. 11 is a flow chart of the control operation of the control system of FIG. 3.

FIG. 11 is a flow chart showing the operation of the control system according to the present invention. At Step I, the CPU is reset and all circuits are started. At Step II, the parameters are entered by way of the keyboard and checked to insure proper and complete input. If the response is NO, enter return back to II. If YES, Step III begins and signal sampling is executed. At Step IV, a check is made to assure that the input signal is equal to (or greater) than current parameters. If the response is NO, let the E.S.U. continue to be on at Step VI and return to Step III. If YES, then leave the alarm circuit ON at Step V and let the output power of the ESU be cut off.

Figure 12:
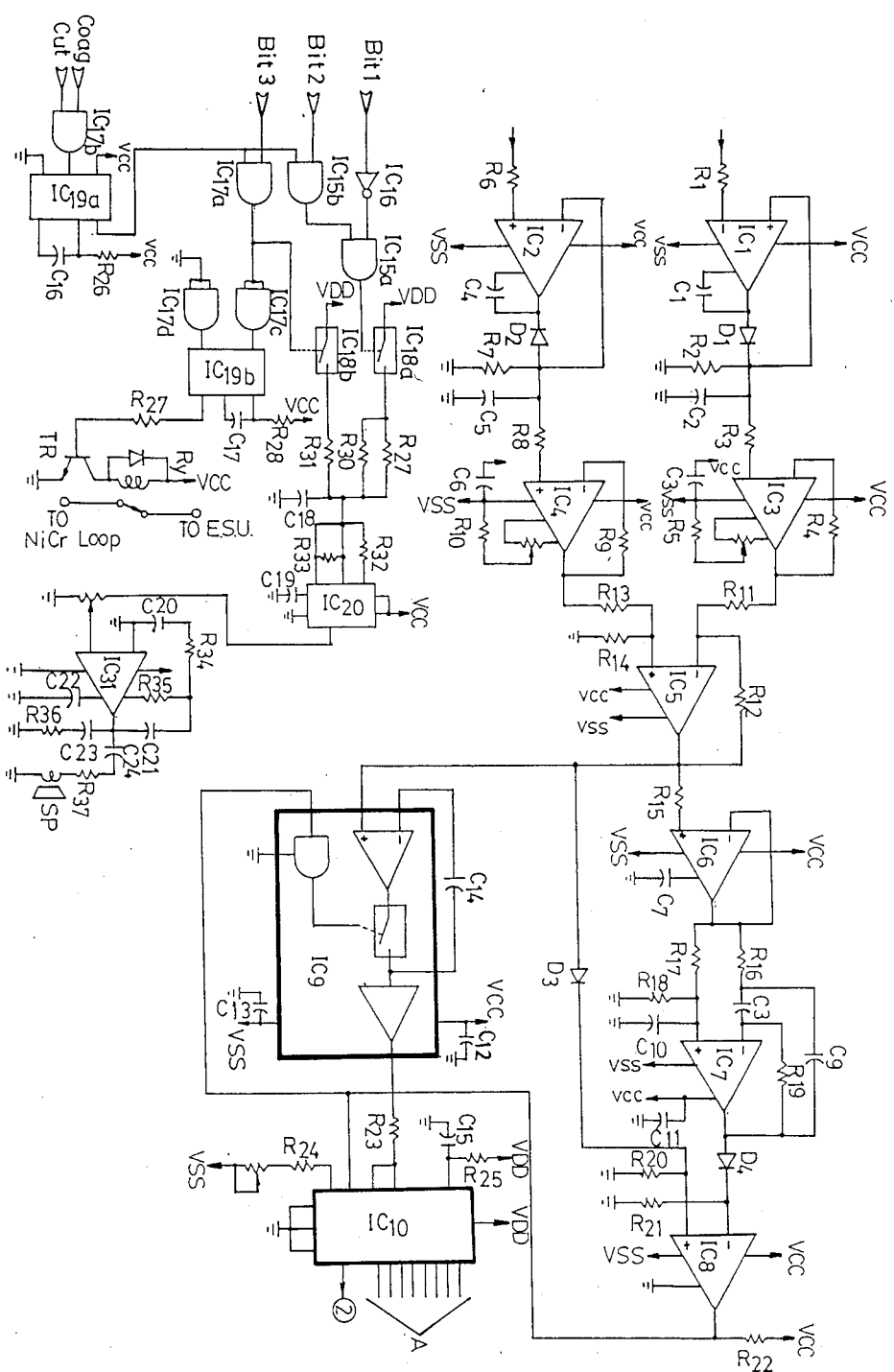
FIG. 12 and 13 are circuit diagrams of the embodiment of the control system of FIG. 3, illustrating, in combination, the circuitry comprising those circuits shown in FIGS. 4–10.
Figure 13:
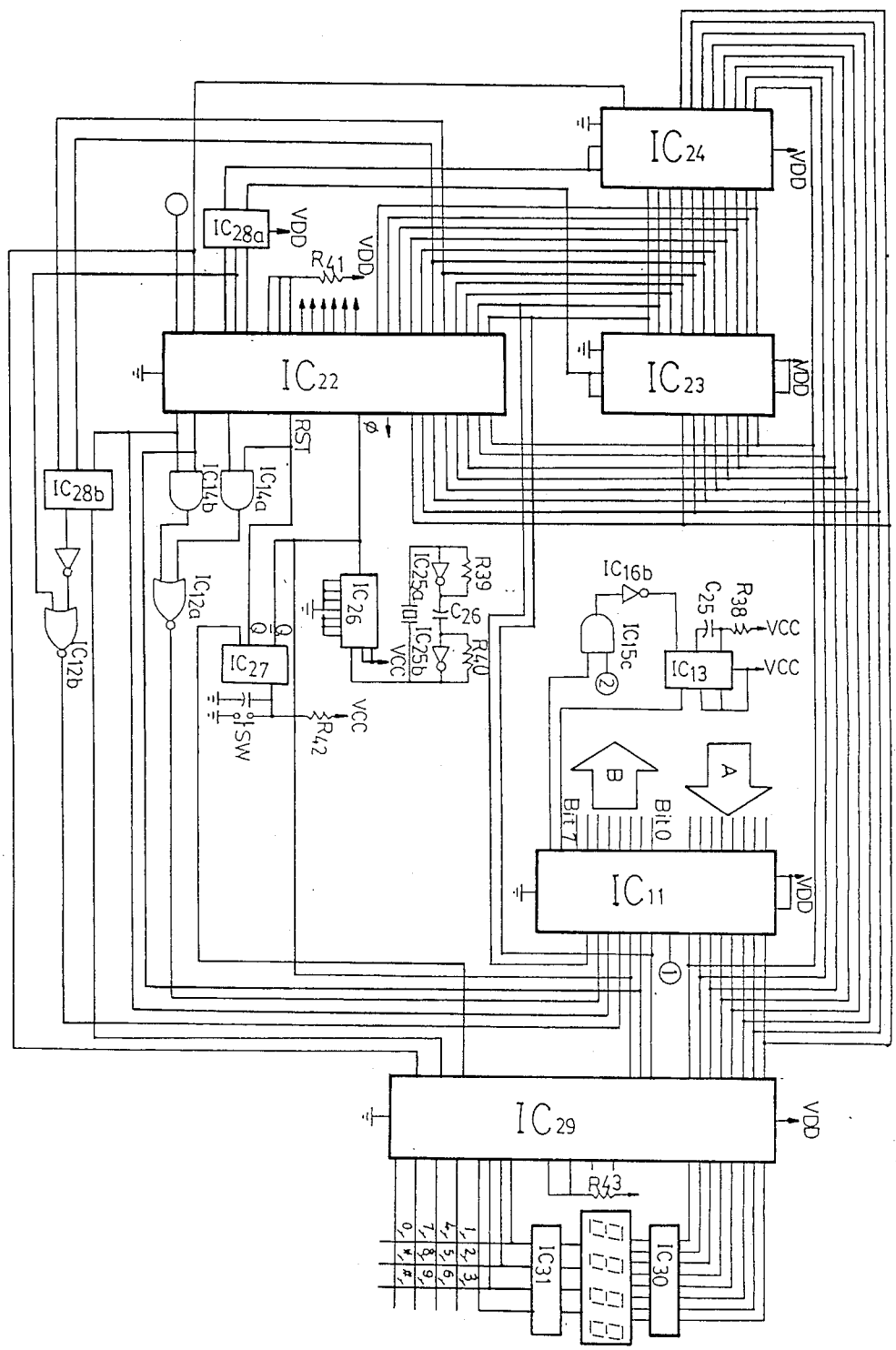

FIGS. 12 and 13 are circuit diagrams of the embodiment of the control system of FIG. 3 and illustrate, in combination, the circuitry of FIGS. 4–10. A detailed description of these circuits have been given previously and will be omitted in this section.

We claim:

1. A control system in combination with an electrosurgical unit, comprising:
   a means for controlling current flow;
   an output electrode and a return electrode;
   a means for distinguishing between different tissue types between said output electrode and said return electrode according to an electrical impedance presented by different tissue types betwen said output electrode and said return electrode;
   said output electrode being adapted to penetate into tissue;
   said means for distinguishing between different tissue types including a means for measuring electrical impedance between said output electrode and said return electrode, and a means for comparing said electrical impedance with predetermined values for said electrical impedance; said predetermined values corresponding to at least two different impedances; and
   said means for comparing producing an output signal based upon comparison of said electrical impedance with said predetermined values of impedance;
   said means for measuring including a current sensing mechanism, including a current probe, said current probe being coupled with an output cable of an electrosurgical unit, said current sensing mechanism producing a signal with an amplitude that is proportional to impedances which occur due to different loads between said two electrodes;
   whereby penetration of said output electrode into one of said at least two tissue types corresponds to one of said predetermined values of impedance, and penetration of said output electrode into another one of said at least two tissue types corresponds to another one of said predetermined values of impedance.

2. The control system according to claim 1, wherein said means for comparing including a peak detection device which receives said signal produced by said current probe, said peak detection device supplying a second signal to corresponding to the amplitude of said signal from said current probe;
   said means for comparing including a phase shifter and level detection device which receives said signal from said current sensing mechanism and produces a timing signal; a Sample/Hold circuit which receives a signal from said peak detection device and from said timing signal, and gives a stable signal, said timing signal triggering said Sample/Hold circuit; and a microprocessor which processes and compares said stable signal to said predetermined values of impedance which are stored in memory and provides two control signals: a first control signal which controls a relay circuit;
   an alarm circuit which receives said first control signal and provides audible signals responsive to said first control signal indicating predetermined load conditions existing between two electrodes; and a relay mechanism which receives said second control signal and provides a third signal responsive to said second control signal for controlling current to said output electrode; whereby penetration of said output electrode into a predetermined tissue type can cause an audible alarm to be produces and can cause current to said output electrode to be controlled.

3. The control system, according to claim 2, further comprising an alarm mechanism which receives a first signal from said microprocessor in response to different loads between said two electrodes, and produces signals which indicate to the user of the electrosurgical unit which different type of load is present.

4. The control system according to claim 2 wherein said peak detection device further comprises:
   four operational amplifiers, said operational amplifiers arranged in two sets of a buffer operational amplifier and amplifying operational amplifier in series for operating on and processing of both a noninverting input and so on inverting input; a summing operational amplifier having as its two inputs the output of said amplifying operational amplifiers for said noninverting input and said inverting input.

5. The control system according to claim 2 wherein said phase shifter and level detection device further comprises:
   a buffer OP amp having an input and which receives as an input signal the output of said peak detection device;
   a phase shifter OP Amp having an output and which receives as an input signal the output of said buffer OP Amp;
   a comparator OP Amp having an input and an output, and which receives as input the output of said phase shifter OP Amp.

6. The control system according to claim 1, further comprising:
   a cutting means in contact with said output electrode;
   said cutting means being adapted for cutting tissue;
   operation of said cutting means being terminated upon penetration into a predetermined type of tissue by said means for controlling current supplied to said cutting means, said means for controlling current being responsive to said output signal from said means for comparing.

* * * * *